United States Patent
Andrieux et al.

(10) Patent No.: US 12,414,909 B2
(45) Date of Patent: Sep. 16, 2025

(54) POLYSACCHARIDE-BASED GELLED FOAM

(71) Applicants: URGO RECHERCHE INNOVATION ET DEVELOPPEMENT, Chenove (FR); CENTRE NATIONAL DE LA RECHERCHE SCIENTIFIQUE-CNRS-, Paris (FR)

(72) Inventors: Sébastien Andrieux, Strasbourg (FR); Wiebke Drenckhan-Andreatta, Strasbourg (FR)

(73) Assignees: URGO RECHERCHE INNOVATION ET DEVELOPPEMENT, Chenove (FR); CENTRE NATIONAL DE LA RECHERCHE SCIENTIFIQUE—CNRS-, Paris (FR)

( * ) Notice: Subject to any disclaimer, the term of this patent is extended or adjusted under 35 U.S.C. 154(b) by 798 days.

(21) Appl. No.: 17/772,676

(22) PCT Filed: Oct. 27, 2020

(86) PCT No.: PCT/FR2020/051940
§ 371 (c)(1),
(2) Date: Apr. 28, 2022

(87) PCT Pub. No.: WO2021/084200
PCT Pub. Date: May 6, 2021

(65) Prior Publication Data
US 2022/0370329 A1    Nov. 24, 2022

(30) Foreign Application Priority Data
Oct. 28, 2019 (FR) ..................... 1912059

(51) Int. Cl.
| | |
|---|---|
| *A61K 47/36* | (2006.01) |
| *A23L 29/256* | (2016.01) |
| *A23P 30/40* | (2016.01) |
| *A61K 8/73* | (2006.01) |
| *A61Q 19/00* | (2006.01) |

(52) U.S. Cl.
CPC ............ *A61K 8/733* (2013.01); *A23L 29/256* (2016.08); *A23P 30/40* (2016.08); *A61K 47/36* (2013.01); *A61Q 19/00* (2013.01); *A23V 2002/00* (2013.01); *A61K 2800/48* (2013.01)

(58) Field of Classification Search
CPC .......... A61K 8/733; A61K 47/36; A23P 30/40
See application file for complete search history.

(56) References Cited

U.S. PATENT DOCUMENTS 7,128,929 B1    10/2006    Scherr

FOREIGN PATENT DOCUMENTS

| CA | 2006882 A1 | 7/1990 |
|---|---|---|
| EP | 0537999 A2 | 4/1993 |
| WO | 9400512 A1 | 1/1994 |
| WO | 2004073697 A1 | 9/2004 |

OTHER PUBLICATIONS

International Search Report (with English Translation) and Written Opinion (with Machine Translation) issued on Jan. 22, 2021 in corresponding International Patent Application No. PCT/FR2020/051940; 14 pages.

*Primary Examiner* — Paul V Ward
(74) *Attorney, Agent, or Firm* — Maier & Maier, PLLC

(57) ABSTRACT

A method for the preparation of a gelled polysaccharide foam, which includes the following steps: (a) the preparation of a mixture including at least one solubilized polysaccharide chosen from alginates, pectic substances, carrageenans, and mixtures thereof, at least one solvent of the polysaccharide, at least one ionic crosslinking agent of the polysaccharide, the crosslinking agent being not available, optionally a plasticizer soluble into the solvent, optionally a surfactant, and optionally an additive, (b) foaming and gelling the mixture prepared at step (a) by incorporating a pH modifying gas, and (c) optionally drying the gelled foam obtained at step (b). Also, the gelled foam obtained from such a method as well as the uses thereof.

20 Claims, No Drawings

POLYSACCHARIDE-BASED GELLED FOAM

The present invention relates to a gelled foam based on polysaccharide. More specifically, the object of the invention is a mixture allowing obtaining such a gelled foam, a method for the preparation of such a gelled foam, the gelled foam obtained thereby, and the uses thereof.

FIELD

The present invention can find applications in the biomedical field, such as, for example, in filling and/or treating wounds, controlled releasing of active agents, in the food industry and in the cosmetic industry.

BACKGROUND

Polysaccharide foams, such as for example alginate foams, have been described for applications such as wound dressings, controlled release delivery systems, cell culture, barrier media to prevent adhesion of bioresorbable tissues and implants. To obtain a stable foam from polysaccharides in solution, a foaming step followed by a crosslinking (covalent or ionic) step is necessary. The crosslink density can be controlled very precisely. However, the toxicity of covalent crosslinking agents pushes towards ionic crosslinking for the implementation of polysaccharide foams in the medical, food or cosmetic fields.

The foaming step can be carried out chemically, for example by means of a foaming agent, or physically, by means of a mixer, or any other expansion system, or by incorporation of gas, for example by means of a siphon.

The ionic gelation requires partial ionic crosslinking of said polysaccharide by means of a solubilized polyvalent counterion. Indeed, the soluble salt (coming from the solubilized polyvalent counterion) complexes with the carboxylate groups of the solubilized polysaccharide to form a polysaccharide gel that is insoluble in a physiological medium.

To obtain a polysaccharide gel that is homogeneous in volume, it is suitable to homogeneously mix the polyvalent counterions within the solubilized polysaccharide before triggering the ionic crosslinking. Indeed, the association kinetics of the polyvalent counterions with the solubilized polysaccharide (for example alginate) is very rapid (instantaneous on a human scale). It is therefore necessary to avoid the ion complexation reaction between the polyvalent counter-ion (generally a metal ion) and the solubilized polysaccharide (for example alginate) while they are being mixed with each other, and to trigger gelation only once the compounds are mixed in a homogeneous way. To control this reaction, two methods are commonly implemented in the literature.

A first method consists in introducing polyvalent counterions in insoluble form. For example, metal cations such as calcium ions can be introduced in the form of a calcium carbonate powder, which can be homogenized within the polysaccharide (alginate) in solution. The polyvalent cation can then be dissolved by adjusting the pH of the solution, usually by acidification. In the case of calcium carbonate, adding acid causes its dissociation into calcium ions and carbonate ions, said divalent calcium ions allowing the ionic crosslinking of the polysaccharide. The gelation kinetics of the polysaccharide is solely dictated by the control of the acidity of the medium and the dissolution kinetics of the calcium carbonate in an acid medium.

A second method consists in using metal cations, such as dissolved calcium ions, in complexed form. The metal cation complex can for example be obtained by means of a chelating agent such as EGTA (egtazic acid) or EDTA (ethylenediaminetetraacetic acid), HEDTA (N-(2-hydroxyethyl) ethylenediaminetriacetic acid), DTPA (diethylene triamine penta acetic acid) or sodium citrate. The calcium ion complex solution can then be mixed with the polysaccharide (alginate) solution, or the alginate can be directly dissolved in the metal ion complex solution. No crosslinking takes place because complexed metal ions are not available. Chelated metal ions can be released by acidifying the medium to reprotonate the chelating agent, and trigger crosslinking. The dissociation of the metal ions and the chelating agent is instantaneous, as is the association of the metal ions (calcium) with the alginate to form ionic bonds which constitute the crosslinking points of the hydrogel network. The gelation kinetics of polysaccharide is solely dictated by the acidity of the medium and the dissociation kinetics of the metal ions and of the chelating agent.

Document WO2004/73697 relates to an alginate solution gelled with a di- or trivalent metal cation, and foamed by a chemical reaction using a foaming/effervescent agent such as sodium carbonate or bicarbonate, the solution besides comprising sodium tetraborate to impart flexibility and elasticity thereto. Document WO94/00512 proposes, for example, to prepare an alginate foam by means of mechanical foaming using a mixer. The foam obtained is then stabilized by adding di- or trivalent, soluble or insoluble cations. When they are insoluble, adding acid allows the dissolution thereof and the dissociation of polyvalent metal salts. These two documents implement foaming methods by mechanical mixing, making it difficult to use them for in situ applications.

Document CA2006882 describes a foam which forms in situ by mixing two solutions: one containing an aqueous solution of alginate, an insoluble di- or trivalent metal salt and optionally an effervescent agent to aid foaming, the other containing an acid, and optionally also an alginate. When the two solutions are mixed, the acidification of the solution containing the insoluble metal salts induces gelling, and possibly foaming when an effervescent agent is present. This method requires perfect and fast mixing of the solutions, which requires to formulate low viscosity solutions. However, a low initial viscosity of the solutions imposes significant limitations in terms of formulation and compromises as to the mechanical properties of the final system. In addition, the document proposes the implementation of such a system by means of a double-piston syringe with a mixing head, which supposes either a single-use product or the use of disposable sterile mixing heads. Finally, if the foam is intended to be applied to the skin or to a wound, the presence of acid can cause pain, irritation or a rash.

Thus, there is a need for a solution for the preparation of a gelled polysaccharide foam, which is easy to use and not requiring the presence of an acid. Such a system would make it possible to avoid a mixing step before in situ application—which would simplify its implementation—and to free oneself from the costly use of sterile single-use equipment. Moreover, if no acid in liquid form is added to the system, this makes it possible to limit the dilution of the polysaccharide which negatively impacts the mechanical properties of the gelled foam.

Surprisingly, the applicant has found that it was possible to obtain a polysaccharide foam, and in particular alginate foam, homogeneous, stable over time, having good mechanical strength and good absorption capacity, from a unique polysaccharide solution that does not include acid.

SUMMARY

The subject of the invention is thus, according to a first aspect, a method for the preparation of a gelled polysaccharide foam comprising the following steps:
a. the preparation of a mixture comprising:
   at least one solubilized polysaccharide chosen from alginates, pectic substances, carrageenans, and mixtures thereof
   at least one solvent of said polysaccharide,
   at least one ionic crosslinking agent of said polysaccharide, said crosslinking agent being not available
   optionally at least one plasticizer soluble into said solvent,
   optionally at least one surfactant, and
   optionally at least one additive,
b. foaming and gelling said mixture prepared at step a. by incorporating a pH modifying gas, and
c. optionally drying the gelled foam obtained at step b.

According to a second other aspect, the object of the invention is a gelled polysaccharide foam obtained from such a method.

According to a third aspect, the object of the invention is the use of such a gelled foam in the biomedical, food or cosmetics field.

Finally, according to a fourth aspect, the object of the invention is the use of such a gelled foam in the treatment of wounds, in particular cavity wounds, venous ulcers, diabetic foot ulcers, pressure ulcers.

DETAILED DESCRIPTION

The method for preparing a gelled polysaccharide foam according to the invention implements a first preparation step of a mixture, comprising:
   at least one solubilized polysaccharide chosen from alginates, pectic substances, carrageenans, and mixtures thereof
   at least one solvent of said polysaccharide,
   at least one ionic crosslinking agent of said polysaccharide, said crosslinking agent being not available
   optionally at least one plasticizer soluble into said solvent,
   optionally at least one surfactant, and
   optionally at least one additive.

Polysaccharide

The polysaccharide according to the invention is a water-soluble biopolymer chosen from alginates, pectic substances, carrageenans, and mixtures thereof.

Alginates are salts of alginic acid. Alginic acid, which is isolated from seaweed, is a polyuronic acid composed of two uronic acids: D-mannuronic acid and L-guluronic acid. The ratio of mannuronic acid and guluronic acid varies depending on factors such as species of algae, age of the plant, and part of the algae (e.g., stem, leaf).

Alginic acid is substantially insoluble in water. It forms water-soluble salts with alkali metals such as sodium, potassium and lithium, magnesium or ammonium but also with substituted ammonium cations derived from lower amines, such as methylamine, ethanolamine, diethanolamine and triethanolamine. The salts are soluble in aqueous media above pH 4, but are converted to alginic acid when the pH is lowered below about pH 4. A water-insoluble alginate is formed if certain polyvalent cations, in particular calcium, barium, strontium, zinc, copper, aluminum and mixtures thereof are present in the medium in appropriate concentrations.

Pectic substances include pectins and pectates. Pectin is a natural polysaccharide found in the roots, stems, leaves and fruits of various plants, especially the skin of citrus fruits such as limes, lemons, grapefruits and oranges. Pectins contain polymer repeat units derived from D-galacturonic acid.

Carrageenan refers to a group of sulphated galactans extracted from red algae. Carrageenans are linear chains of D-galactopyranosyl units joined with alternating $(1 \rightarrow 3)\alpha$-D and $(1 \rightarrow 4)$ $\beta$-D-glycosidic bonds. Carrageenans can, in part, be distinguished by the degree and position of sulfation. Most sugar units have one or two sulfate groups esterified to a hydroxyl group on the C-2 or C-6 carbons. There are three main types of carrageenan, kappa carrageenan, iota carrageenan and lambda carrageenan. Kappa carrageenans produce strong rigid gels, while those based on iota products are flabby. Lambda carrageenans do not gel in water. A iota carrageenan is preferred.

According to a preferred embodiment, the polysaccharide used in the context of the invention is alginate.

The mixture prepared in step a. generally comprises from 0.5% to 10% by weight, preferably from 1% to 6% by weight, more preferably from 2% to 4% by weight of polysaccharide, preferably alginate.

Preferably, the alginates have a weight-average molecular mass of between 50 000 and 400 000 Da, measured according to the steric exclusion chromatography method.

High molecular weight alginates (between 100 000 and 400 000 Da) can be used alone or in combination with low molecular weight alginates (less than 100 000 Da).

Solvent

The mixture prepared at step a. of the claimed method uses at least one solvent.

These solvents make it possible to dissolve all or part of the ingredients of the mixture.

Preferably, the solvent is inorganic, and advantageously, the solvent is water.

The solvent makes it possible to dissolve or disperse the ingredients of the mixture prepared in step a. The solvent used to form the mixture must not contain ions such as calcium, capable of crosslinking the polysaccharide and forming a gel at the stage of step a. Thus, the solvent is preferably free of divalent ions. More preferably, the solvent can be water. When the solvent used is water, it is preferable to use distilled or deionized water.

In particular, the solvent is present in an amount of 50% to 99% by weight, preferably 80% to 97% by weight, relative to the total weight of the mixture.

Ionic Crosslinking Agent

The mixture prepared at step a. of the claimed method implements at least one agent for ionic crosslinking the polysaccharide, which crosslinking agent is not available.

The ionic crosslinking agent is preferably a polyvalent cation, preferably bi- or trivalent, or a mixture of polyvalent cations capable of ionically crosslinking with the polysaccharide.

According to a preferred embodiment, suitable polyvalent cations include, for example, calcium, barium, strontium, iron, zinc, copper, and aluminum. Preferred cations are divalent metal cations, preferably calcium.

Ionic crosslinking agents can be implemented in the form of salts such as calcium carbonate, calcium disodium edetate, calcium oxalate, dicalcium phosphate, tricalcium phosphate, tricalcium citrate, strontium carbonate, barium carbonate, cupric carbonate, zinc carbonate, zinc oxalate and phosphate, hydrates thereof, and mixtures thereof. Any salt or combination of salts which provides the desired polyvalent cation for crosslinking or a mixture of polyvalent cations can be used as the ionic crosslinking agent.

The ionic crosslinking agent used at step a. of the method of the invention is "not available" (in French: "non disponible") so that the mixture implemented at step a. of the method cannot crosslink the polysaccharide before a pH modifying gas is incorporated. By "not available" crosslinking agent is meant an ionic crosslinking agent which has been neutralized so as not to react with the polysaccharide without adding an activating agent. The crosslinking agent can be rendered not available by being introduced into the mixture in the form of an insoluble compound, or in the form of a complexed compound. The activation of said "not available" crosslinking agent is for example carried out by adjusting the pH by means of a pH modifying agent, in particular by acidification.

The ionic crosslinking agent can be rendered "not available" by introducing it into the mixture of step a. in a form which is insoluble in the solvent (in particular in water), but which can be solubilized, preferably in an acid medium, so as to release the polyvalent cation, so as to ensure that the polysaccharide crosslinks and to form the desired gel. Typically, the polyvalent cation can be released at a pH from 3, in particular between 3 and 6.5.

Alternatively, the ionic crosslinking agent may be soluble in the solvent (particularly in water), but rendered "not available" by complexation using a chelating agent. As in the previous variant, the polyvalent cation can preferably be released under acidic conditions. The chelating agent can for example be chosen from EGTA (egtazic acid) or EDTA (ethylenediaminetetraacetic acid), HEDTA (N-(2-hydroxyethyl) ethylenediaminetriacetic acid), DTPA (diethylene triamine penta acetic acid).

According to a preferred embodiment, the ionic crosslinking agent is a bivalent ion in chelated form.

A preferred crosslinking agent, in particular when the polysaccharide is alginate or chosen from pectic materials and iota carrageenan, is calcium chelated with egtazic acid.

The ionic crosslinking agent is present in an amount of 0.1% to 15% by weight, preferably 1% to 10% by weight, more preferably 2% to 5% by weight, relative to the total weight of the mixture.

Plasticizer

The mixture prepared at step a. of the method can also implement at least one plasticizer, preferably soluble in the solvent, in particular in water.

Thus, according to a preferred embodiment, the mixture prepared at step a. includes a water-soluble plasticizer.

A plasticizer imparts flexibility to the polysaccharide gel foam.

Typical plasticizers are polyhydric alcohols such as glycerin, sorbitol, ethylene glycol, propylene glycol, and polyethylene glycol.

Preferably, the plasticizer is non-toxic and does not modify the solubility of the polysaccharide.

Surfactant

The mixture prepared at step a. of the method can also comprise at least one surfactant, preferably nonionic, as a foaming agent.

The nonionic surfactant can be chosen from
(1) surfactants which are fluid at a temperature lower than or equal to 45° C., chosen from esters having at least one polyol chosen from the group formed by a polyethylene glycol comprising from 1 to 60 ethylene oxide repeat units, sorbitan, glycerol comprising from 2 to 30 ethylene oxide repeat units, polyglycerols comprising from 2 to 12 glycerol repeat units, and at least one fatty acid comprising at least one linear or C8-C22 branched alkyl chain, saturated or unsaturated,
(2) mixed esters of fatty acid or fatty alcohol, carboxylic acid and glycerol,
(3) fatty acid esters of carbohydrates and fatty alcohol ethers of sugars,
(4) surfactants which are solid at a temperature lower than or equal to 45° C., selected from glycerol fatty acid esters, sorbitan fatty acid esters and oxyethylenatedoxyethylenated sorbitan fatty acid esters, ethoxylated fatty acid ethers and ethoxylated fatty acid esters,
(5) block copolymers of ethylene oxide (A) and propylene oxide (B), and
(6) silicone surfactants.

The surfactants (1) which are fluid at a temperature less than or equal to 45° C. can be, in particular:
polyethylene glycol isostearate having a molecular weight of 400;
diglyceryl isostearate, sold by Solvay;
glyceryl laurate comprising 2 glycerol repeat units, marketed by the company Solvay;
sorbitan oletate, marketed under the name Span 80 by the company IC;
sorbitan isostearate, sold under the name Nikkol SI 1OR by Nikko; and
α-butylglucoside cocoate or α-butylglucoside caprate The mixed esters of fatty acid or fatty alcohol (2), carboxylic acid and glycerol, which can be used as the nonionic surfactant above, can be chosen in particular from the group comprising mixed esters fatty acid or fatty alcohol with an alkyl chain containing 8 to 22 carbon atoms, and α-hydroxy acid and/or succinic acid, with glycerol. The α-hydroxy acid can be, for example, citric acid, lactic acid, glycolic acid or malic acid, and mixtures thereof.

The alkyl chain of the fatty acids or alcohols from which the mixed esters are derived which can be used in the emulsion of the invention can be linear or branched, and saturated or unsaturated. It may be, in particular, stearate, isostearate, linoleate, oleate, behenate, arachidonate, palmitate, myristate, laurate, caprate, isostearyl, stearyl, linoleyl, oleyl, behenyl, myristyl, lauryl or capryl chains, and mixtures of thereof.

As examples of mixed esters which can be used in the emulsion of the invention, mention can be made of the mixed ester of glycerol and the mixture of citric acid, lactic acid, linoleic acid and oleic acid (CTFA name: glyceryl citrate/lactate/linoleate/oleate) marketed by the company Hüls under the name Imwitor 375; the mixed ester of succinic acid and of isostearyl alcohol with glycerol (CTFA name: isostearyl-diglyceryl succinate) marketed by the company Hüls under the name Imwitor 780 K; the mixed ester of citric acid and stearic acid with glycerol (CTFA name: glyceryl stearate-citrate) marketed by the company Hüls under the name Imwitor 370; the mixed ester of lactic acid and stearic acid with glycerol (CTFA name: glyceryl stearate-lactate) marketed by Danisco under the name Lactodan B30 or Rylo LA30.

The fatty acid esters of sugars (3), which can be used as the nonionic surfactant above, can preferably be solid at a temperature lower than or equal to 45° C. and can be chosen in particular from the group comprising esters or mixtures of C8-C22 fatty acid esters and saccharose, maltose, glucose or fructose, and esters or mixtures of C14-C22 fatty acid esters and methylglucose.

The $C_8$-$C_{22}$ or $C_{14}$-$C_{22}$ fatty acids forming the fatty acid repeat unit of the esters which can be used in the present invention comprise a saturated or unsaturated linear alkyl chain containing, respectively, from 8 to 22 or from 14 to 22 carbon atoms. The fatty acid repeat unit of the esters can be chosen in particular from stearates, behenates, arachidonates, palmitates, myristates, laurates and caprates, and mixtures thereof. Stearates are preferably used.

As examples of ester or fatty acid ester mixtures with sucrose, maltose, glucose or fructose, mention may be made of sucrose monostearate, sucrose distearate and sucrose tristearate and mixtures thereof, such as the products marketed by the company Croda under the name Crodesta F50, F70, F110 and F160; and examples of ester or fatty acid ester mixtures with methylglucose which can be mentioned are methylglucose-polyglyceryl-3 distearate, marketed by the company Goldschmidt under the name Tego-care 450. Mention may also be made of glucose or maltose monoesters such as methyl-o-hexadecanoyl-6-D-glucoside and o-hexadecanoyl-6-D-maltoside.

The fatty alcohol ethers of sugars (3), which can be used as the nonionic surfactant above, can be solid at a temperature lower than or equal to 45° C. and can be chosen in particular in the group comprising ethers or mixtures of C8-C22 fatty alcohol ethers and glucose, maltose, sacchar-ose or fructose, and ethers or mixtures of ethers of a C14-C22 fatty alcohol and methylglucose. These are in particular alkylpolyglucosides.

The $C_8$-$C_{22}$ or $C_{14}$-$C_{22}$ fatty alcohols forming the fatty acid repeat unit of the ethers which can be used comprise a linear saturated or unsaturated alkyl chain containing, respectively, from 8 to 22 or from 14 to 22 carbon atoms. The fatty acid repeat unit of the ethers can be chosen in particular from decyl, cetyl, behenyl, arachidyl, stearyl, palmityl, myristyl, lauryl, capryl and hexadecanoyl repeat units, and mixtures thereof, such as cetearyl.

As examples of fatty alcohol ethers of carbohydrates, mention may be made of alkylpolyglucosides such as decylglucoside and laurylglucoside, which is marketed, for example, by the company Henkel under the respective names Plantaren 2000 and Plantaren 1200, cetostearyl glucoside optionally in the form of a mixture with cetostearyl alcohol, marketed for example under the name Montanov 68 by the company SEPPIC, under the name Tego-care CG90 by the company Goldschmidt and under the name Emulgade KE3302 by the company Henkel, as well as arachidyl-glucoside, for example in the form of a mixture of arachidyl alcohol and behenyl alcohol and arachidyl glucoside, marketed under the name Montanov 202 by the company SEPPIC.

The used surfactant is more particularly sucrose monostearate, saccharose distearate or saccharose tristearate and mixtures thereof, methylglucose-polyglyceryl-3 distearate and alkylpolyglucosides.

The glycerol fatty acid esters (4) which can be used as the above nonionic surfactant, which are solid at a temperature lower than or equal to 45° C., can be chosen in particular from the group comprising esters formed from at least one acid comprising a saturated linear alkyl chain containing from 12 to 22 carbon atoms and from 1 to 12 glycerol repeat units.

These esters can be chosen in particular from glycerol stearates, behenates, arachidates and palmitates, and mixtures thereof.

As examples of surfactants which can be used in the present invention, mention may be made of decaglyceryl monostearate, distearate, tristearate and pentastearate (CTFA names: polyglyceryl-10 stearate, polyglyceryl-10 distearate, polyglyceryl-10 tristearate, polyglyceryl-10 pentastearate), such as the products marketed under the respective names Nikkol Decaglyn 1 S, 2 S, 3 S and 5 S by the company Nikko, and diglyceryl monostearate (CTFA name: polyglyceryl-2 stearate), such as the product marketed by the company Nikko under the name Nikkol DGMS.

The sorbitan fatty acid esters (4) which can be used as the above nonionic surfactant, which are solid at a temperature lower than or equal to 45° C., can be selected from the group comprising C16-C22 fatty acid esters of sorbitan and oxyethylenatedoxyethylenated C16-C22 fatty acid esters of sorbitan. They are formed from at least one fatty acid comprising at least one saturated linear alkyl chain containing, respectively, from 16 to 22 carbon atoms, and from sorbitol or ethoxylated sorbitol. The oxyethylenatedoxyethylenated esters generally comprise from 1 to 100 ethylene glycol repeat units and preferably from 2 to 40 ethylene oxide (EO) repeat units.

These esters can be chosen in particular from stearates, behenates, arachidates, palmitates, and mixtures thereof.

As examples of the above nonionic surfactant which can be used in the present invention, mention may be made of sorbitan monostearate (CTFA name: sorbitan stearate), marketed by the company ICI under the name Span 60, sorbitan monopalmitate (CTFA name: sorbitan palmitate), marketed by the company ICI under the name Span 40, and sorbitan tristearate 20 EO (CTFA name: polysorbate 65), marketed by the company ICI under the name Tween 65.

The ethoxylated fatty acid ethers (4) which are solid at a temperature lower than or equal to 45° C., which can be used as the above nonionic surfactant, are preferably ethers formed from 1 to 100 repeat units of ethylene oxide and at least one fatty alcohol chain containing 16 to 22 carbon atoms. The fatty chain of the ethers can be chosen in particular from behenyl, arachidyl, stearyl and cetyl repeat units, and mixtures thereof, such as cetearyl. Examples of ethoxylated fatty acid ethers that may be mentioned are behenyl alcohol ethers comprising 5, 10, 20 and 30 ethylene oxide repeat units (CTFA names: beheneth-5, beheneth-10, beheneth-20, beheneth-30), such as the products marketed under the names Nikkol BBS, BB10, BB20 and BB30 by the company Nikko, and stearyl alcohol ether comprising 2 ethylene oxide repeat units (CTFA name: steareth-2), such as the product marketed under the name Brij 72 by the company ICI.

The ethoxylated fatty acid esters (4) which are solid at a temperature lower than or equal to 45° C., which can be used as the above nonionic surfactant, are esters formed from 1 to 100 repeat units of ethylene oxide and at least one fatty acid chain containing 16 to 22 carbon atoms. The fatty chain in the esters can be chosen in particular from stearate, behenate, arachidate and palmitate repeat units, and mixtures thereof. Examples of ethoxylated fatty acid esters which may be mentioned are stearic acid ester comprising 40 ethylene oxide repeat units, such as the product marketed under the name Myrj 52 (CTFA name: PEG-40) by the company ICI, as well as the behenic acid ester comprising 8 ethylene oxide repeat units (CTFA name: PEG-8 behenate), such as the product marketed under the name Compritol HD5 ATO by the company Gattefosse.

The block copolymers of ethylene oxide (A) and of propylene oxide (B) (5), which can be used as surfactants according to the invention, can be chosen in particular from block copolymers of formula (IV): $HO(C_2H_4O)x(C_{3H-160})_y(C_2H_4O)_zH$ where x, y and z are integers such that x+z is in the range 2 to 100 and y is in the range 14 to 60, and mixtures thereof, and more particularly among block copolymers of formula (IV) having an HLB value in the range of 8.0 to 14.0.

The silicone surfactant (6) as nonionic surfactant above can preferably be chosen from those marketed by the company Dow Corning under the names DC 5329, DC 7439-146, DC 2-5695 and Q4-3667.

According to a preferred embodiment, the nonionic surfactant used in the mixture of step a. has an HLB value of 8.0 to 14.0, preferably 9.0 to 13.5, and more preferably 10.0 to 13.0.

Such a nonionic surfactant is preferably chosen from:
polyethylene glycol isostearate or oleate (8 to 10 moles of ethylene oxide),
polyethylene glycol isocetyl, behenyl ether or isostearyl ether (8 to moles of ethylene oxide),
polyglyceryl monolaurate or dilaurate comprising 3 to 6 glycerol repeat units,
polyglyceryl mono(iso)stearate comprising 3 to 6 glycerol repeat units,
polyglyceryl monooleate comprising 3 to 6 glycerol repeat units, and
polyglyceryl dioleate comprising 3 to 6 glycerol repeat units.

According to a preferred embodiment of the present invention, the nonionic surfactant having an HLB value of 8.0 to 14.0, preferably 9.0 to 13.5, and more preferably 10.0 to 13.0, is selected from polyglyceryl fatty acid esters and mono- or poly-oxyethylenated fatty acid esters.

It is preferable that the polyglyceryl fatty acid ester comprises esters of a fatty acid and polyglycerin containing 70% or more of polyglycerin whose degree of polymerization is 4 or more, preferably esters of a fatty acid and polyglycerine containing an amount equal to or greater than 60% of polyglycerine whose degree of polymerization is between 4 and 11, and more preferably esters of a fatty acid and polyglycerine containing an amount equal to or greater than 30% polyglycerine whose degree of polymerization is 5.

The polyglyceryl fatty acid ester can be chosen from mono, di and tri-esters of saturated or unsaturated acid, preferably a saturated acid, comprising 2 to 30 carbon atoms, preferably 6 to 30 carbon atoms, and more preferably 8 to carbon atoms, such as lauric acid, oleic acid, stearic acid, isostearic acid, capric acid, caprylic acid, and myristic acid.

It is preferred that the polyglyceryl fatty acid ester be selected from the group consisting of PG-4 laurate, PG-5 laurate, PG-5 dilaurate, PG-5 oleate, PG-5 dioleate, PG-6 tricaprylate, PG-5 myristate, PG-5 trimyristate, PG-5 stearate, PG-5 isostearate, PG-5 trioleate, PG-6 caprylate, and PG-6 tricaprylate.

It is preferred that the mono- or poly-oxyethylene fatty acid ester have a (poly)oxyalkylene section derived from 1 to 20 oxyalkylenes, preferably 3 to 15 oxyalkylenes, and more preferably 8 to 10 oxyalkylenes.

The oxyalkylene section can be derived from alkylene glycols such as ethylene glycol, propylene glycol, butylene glycol, pentylene glycol, hexylene glycol, and the like. The oxyalkylene section can contain a number of moles of ethylene oxide and/or propylene oxide of between 1 and 100 and preferably between 2 and 50. Advantageously, the nonionic surfactants do not include oxypropylene repeat units.

The mono- or poly-oxyethylenated fatty acid ester can be chosen from mono and di-esters of saturated or unsaturated acid, preferably a saturated acid, comprising from 2 to 30 carbon atoms, preferably from 6 to 30 carbon atoms, and more preferably from 8 to 30 carbon atoms, such as lauric acid, oleic acid, stearic acid, isostearic acid, capric acid, caprylic acid, and myristic acid.

Examples of mono- or poly-oxyethylenated fatty acid esters which may be mentioned include $C_2$-$C_{30}$, preferably $C_6$-$C_{30}$ and more preferably $C_8$-$C_{22}$ linear or branched, saturated or unsaturated acid esters of polyethylene glycols.

Examples of mono- or poly-oxyethylenated fatty acid esters which may be mentioned include adducts of ethylene oxide with esters of lauric acid, myristic acid, palmitic acid, stearic acid, isostearic acid, oleic acid or behenic acid, and mixtures thereof, in particular those containing from 8 to 30 oxyethylene groups, such as PEG-8 to PEG-30 laurate (under the CTFA names: PEG-8 laurate to PEG-30 laurate); myristate from PEG-8 to PEG-30 (under the CTFA names: PEG-8 myristate to PEG-30 myristate); palmitate from PEG-8 to PEG-30 (under the CTFA names: PEG-8 palmitate to PEG-30 palmitate); PEG-8 to PEG-30 stearate (under the CTFA names: PEG-8 stearate to PEG-30 stearate); isostearate from PEG-8 to PEG-30 (under the CTFA names: PEG-8 isostearate to PEG-30 isostearate); oleate from PEG-8 to PEG-30 (under the CTFA names: PEG-8 oleate to PEG-30 oleate); behenate from PEG-8 to PEG-30 (under the CTFA names: PEG-8 behenate to PEG-30 behenate); and mixtures thereof.

Preferably, the polyglycol fatty acid ester is selected from the group consisting of PEG-8 isostearate, PEG-8 stearate, PEG10 isostearate, PEG10 oleate, ether isocetyl of PEG10, behenyl ether of PEG10 or isostearyl ether of PEG10 and a mixture thereof.

Among the anionic surfactants that can be used, alone or in mixtures, in the context of the present invention, mention may be made in particular (non-limiting list) of salts (in particular alkaline salts, in particular sodium salts, ammonium salts, amine salts, aminoalcohol salts or magnesium salts) of the following compounds: alkyl sulphates, alkyl ether sulphates, alkylamido ether sulphates, alkylarylpolyether sulphates, monoglyceride sulphates; alkylsulfonates, alkylphosphates, alkylamidesulfonates, alkylarylsulfonates, α-olefin-sulfonates, paraffin-sulfonates; alkylsulfosuccinates, alkylethersulfosuccinates, alkylamidesulfosuccinates; alkyl sulfosuccinamates; alkylsulfoacetates; alkyl ether phosphates; acylsarcosinates; acylisethionates and N-acyltaurates, the alkyl or acyl radical of all these various compounds preferably comprising from 12 to 20 carbon atoms, and the aryl radical preferably designating a phenyl or benzyl group. Among the anionic surfactants which can also be used, mention may also be made of the salts of fatty acids such as the salts of oleic, ricinoleic, palmitic and stearic acids, the copra oil or hydrogenated copra oil acids; acyl-lactylates whose acyl radical comprise 8 to 20 carbon atoms. It is also possible to use weakly anionic surfactants, such as alkyl D galactoside uronic acids and the salts thereof as well as polyoxyalkylenated alkyl (C6-C24) ether carboxylic acids, polyoxyalkylenated alkyl (C6-C24) aryl ether carboxylic acids, polyoxyalkylenated alkyl (C6-C24) amido ether carboxylic acids and salts thereof, in particular those comprising from 2 to 50 ethylene oxide groups, and mixtures thereof.

An anionic surfactant chosen from sodium, triethanolamine or ammonium (C12-C14) alkyl sulphates, sodium (C12-C14) alkyl ether sulphates oxyethylenated with 2.2 moles of ethylene oxide, sodium cocoyl isethionate and sodium alpha-olefin (C14-C16) sulfonate, is preferably used.

Among the anionic surfactants, according to the invention, the use of the salts of alkyl sulphates and of alkyl ether sulphates and mixtures thereof is preferred.

The surfactant is preferably present in an amount of 0.01% to 10% by weight, preferably 0.05% to 5% by weight, more preferably 0.1% to 2% by weight, relative to the total weight of the mixture.

Additives

The composition according to the invention may comprise one or more pharmaceutically acceptable additives, such as, for example, perfumes, flavorings, colorings, pigments, matting agents, rheological agents, antifoam agents, preservatives, vitamins, essential oils and active agents, in particular selected from antibacterial agents, antiseptics, antivirals, antifungal agents, painkillers, anti-inflammatory agents, agents promoting cicatrization, moisturizing agents, depigmenting agents, keratolytic agents, restructuring active agents, anesthetics and solar filters.

In particular, the active agents which can be introduced into the composition according to the invention can be selected from:

- anti-bacterials such as Polymyxin B, penicillins (Amoxycillin), clavulanic acid, tetracyclines, Minocycline, chlorotetracycline, aminoglycosides, Amikacin, Gentamicin, Neomycin, silver and salts thereof (silver sulfadiazine), probiotics;
- antiseptics such as sodium mercurothiolate, eosin, chlorhexidine, phenylmercury borate, hydrogen peroxide, Dakin's solution, triclosan, biguanide, hexamidine, thymol, Lugol, Povidone iodine, Merbromine, Benzalkonium and Benzethonium Chloride, ethanol, isopropanol;
- anti-virals such as Aciclovir, Famciclovir, Ritonavir;
- antifungals such as polyenes, Nystatin, Amphotericin B, Natamycin, imidazoles (Miconazole, Ketoconazole, Clotrimazole, Econazole, Bifonazole, Butoconazole, Fenticonazole, Isoconazole, Oxiconazole, Sertaconazole, Sulconazole, Thiabendazole, Tioconazole), triazoles (Fluconazole, Itraconazole, Ravuconazole, Posaconazole, Voriconazole), allylamines, Terbinafine, Amorolfine, Naftifine, Butenafine;

Flucytosine (antimetabolite), Griseofulvin, Caspofungin, Micafungin;

- painkillers such as Paracetamol, Codeine, Dextropropoxyphene, Tramadol, Morphine and derivatives thereof, Corticosteroids and derivatives;
- anti-inflammatory agents such as Glucocorticoids, non-steroidal anti-inflammatory agents, Aspirin, Ibuprofen, Ketoprofen, Flurbiprofen, Diclofenac, Aceclofenac, Ketorolac, Meloxicam, Piroxicam, Tenoxicam, Naproxen, Indomethacin, Naproxcinod, Nimesulide, Celecoxib, Etoricoxib, Parecoxib, Rofecoxib, Valdecoxib, Phenylbutazone, niflumic acid, mefenamic acid;
- active agents promoting cicatrization such as Retinol, Vitamin A, Vitamin E, N-acetyl-hydroxyproline, Centella Asiatica extracts, papain, silicones, essential oils of thyme, niaouli, rosemary, tea tree and sage, hyaluronic acid, synthetic polysulfated oligosaccharides having 1 to 4 ose units such as potassium salt of octasulfated sucrose, silver salt of octasulfated sucrose or sucralfate, metformin, Allantoin;
- moisturizing agents such as hyaluronic acid, urea, glycerol, fatty acids, aquaporin modulators, vegetable oils, chitosan, certain sugars including sorbitol, butters and waxes;
- depigmenting agents such as kojic acid (KojicAcid SL®-Quimasso (Sino Lion)), Arbutin (Olevatin®-Quimasso (Sino Lion)), the mixture of sodium palmitoylpropyl and white water lily extract (Sepicalm®-Seppic), undecylenoyl phenylalanine (Sepiwhite®-Seppic), liquorice extract obtained by fermentation of *Aspergillus* and ethoxydiglycol (GatulineWhitening®-Gattefossé), octadecenedioic acid (ODA White®-Sederma), alpha-arbutin (Alpha-arbutin®, SACI-CFPA (Pentapharm)), the aqueous extract of Arctophylos Uva Ursi leaves (Melfade-J®-SACI-CFPA (Pentapharm)), the complex plant mixture Gigawhite® (SACI-CFPA (Alpaflor)), diacetylboldine (Lumiskin®-Sederma), Japanese mandarin extract (Melaslow®-Sederma), the mixture of lemon extract enriched with citric acid and cucumber extract (Uninontan® U-34-Unipex), the mixture of *Rumex occidentalis* extract and vitamin C (Tyrostat® 11-Unipex), oligopeptides (Mélanostatin 5®-Unipex), I e dipalmitatekojique (KAD-15®-Quimasso (Sino Lion)), the complex of natural origin Vegewhite® from LCW, wheat germ extracts (Clariskin® II-Silab), ethyldiaminetriacetate (EDTA);
- keratolytic agents such as salicylic acid, zinc salicylate, ascorbic acid, alpha hydroxy acids (glycolic, lactic, malic, citric, tartaric acid), extracts of silver maple, sour cherry, tamarind, urea, the topical retinoid Kératoline® (Sederma), proteases obtained by fermentation of *Bacillus Subtilis*, the product Linked-Papain® (SACI-CFPA), papain (proteolytic enzyme from *papaya* fruit);
- restructuring active agents (for example restructuring the skin appendages) such as silica derivatives, vitamin E, chamomile, calcium, horsetail extract, silk lipester;
- anesthetics such as benzocaine, lidocaine, dibucaine, pramoxine hydrochloride, bupivacaine, mepivacaine, prilocaine, etidocaine;
- solar filters, such as chemical filters (Oxybenzone, Sulisobenzone, Dioxybenzone, Tinosorb S®, Avobenzone, 2-ethoxyethyl p-methoxycinnamate, Uvinul® A+, Mexoryl® XL, Octyl methoxycinnamate or octinoxate, Octyl salicylate or octisalate, octyl triazone or Uvinul® T 150, methyl salicylate, meradimate, enzacamene, MBBT or Tinosorb® M, octyl cyanophenylcinnamate or Parsol® 340, Para-aminobenzoic acid, Ensulizole, Parsol® SLX or Polysiloxane-15 or Benzylidenemalonatepolysiloxane, triethanolamine salicylate or trolamine salicylate, Mexoryl® SX or terephthalylidene dicamphosulphonic acid) and mineral filters (zinc oxides, titanium dioxide, kaolin, ichthyol).
- dispersing agents for mineral salts (calcium carbonate and others) marketed by Byk (for example BYK-154), or ICL Advanced Additives (under the Calgon® and Lopon® trademarks).

Antifoam agents can be:

- oil-based (mineral oil, vegetable oil, white oil or any other oil insoluble in the foaming medium). An oil based antifoam agent may also contain hydrophobic silica and/or wax to improve its performance. Typical waxes are ethylene bis stearamide, paraffin waxes, ester waxes and fatty alcohol waxes.
- in powder form. Powder antifoam agents are in principle oil-based antifoam agents on a particulate carrier such as silica.
- water-based (different types of oils and waxes dispersed in a water base). The oils are often mineral oils or vegetable oils and the waxes are long chain fatty alcohols, fatty acid soaps or esters.

silicone-based (polymers with a silicon skeleton). These can be in the form of an oil- or water-based emulsion. The silicone compound consists of a hydrophobic silica dispersed in a silicone oil. Emulsifiers are added so that the silicone spreads quickly and well in the foaming medium. The silicone compound may also contain silicone glycols and other fluids based on modified silicone. Polydimethylsiloxane is a widely used antifoam agent.

based on copolymers of polyethylene glycol and polypropylene glycol. They come in the form of oils, aqueous solutions or water-based emulsions.

based on alkyl polyacrylates.

The additive may be present in an amount of 0.5% to 20% by weight, preferably 0.5% to 5% by weight, more preferably 1% to 5% by weight, relative to the total weight of the mixture.

Gelling and Foaming the Polysaccharide

The method according to the invention implements a second step b. of foaming and gelling said mixture prepared at step a. by incorporating a pH modifying gas.

Such a pH modifying gas is preferably an acid gas.

Indeed, in the context of the present invention, the gas used during step b. is a gas capable of acidifying the medium.

Among the gases capable of acidifying the medium, mention may be made, by way of example, of carbon dioxide, sulfur dioxide, nitrogen oxide.

According to a particular embodiment, step b. can be implemented by incorporating a mixture of an acid gas with an inert gas.

Preferably carbon dioxide or a gas mixture containing carbon dioxide is used.

The presence of this gas in the bubbles of the foam will induce the triggering of the system gelation by foaming. Gelation is triggered by the dissolution of the gas present in the bubbles in the liquid phase of the foam, which, by chemical reaction, acidifies the medium and releases the polyvalent cations (either by dissolution of a metallic salt introduced in an insoluble form, or by reprotonation of chelating agents of said salt) allowing the ionic crosslinking of the polysaccharide. Moreover, since foaming induces gelation, the invention allows control of the formation kinetics of the hydrogel without the addition of an acidifying agent being needed, which would dilute the polymer matrix. Finally, the use of gases to induce gelation is an advantage due to their chemical stability and low toxicity. The use of gas makes it possible to initiate gelation at the surface of the bubbles, and therefore to promote the formation of closed-cell foams. On the contrary, the gelation obtained by the techniques of the prior art is ordinarily initiated in the core of the liquid phase.

The foaming is preferably physical and non chemical foaming.

People familiar with the field of liquid foams will be able to modify the gelation kinetics by controlling the quantity of acid gas dissolved the liquid phase. This control can be carried out by:

modifying the acid gas/inert gas ratio in the foaming gas mixture, incorporating of a perfluorinated hydrocarbon, for example perfluorohexane, into the gas phase, which by balancing the chemical potentials between the bubbles will limit the dissolution of the acidifying gas into the liquid phase, and in fact will slow down and/or limit gelation, modifying the size of the bubbles, insofar as the pressure inside a bubble is all the more important as the bubble is small. The small bubbles will then favor the dissolution of the acidifying gas into the liquid phase, and in fact a faster gelling.

A gelled foam can be prepared at step b. by incorporating a pH modifying gas, using micro- or milli-fluidic methods.

A spray system containing an acid gas such as carbon dioxide as a propellant can also be used for in situ application.

Another method consists in using a siphon, of the kitchen siphon type, with cartridges of carbon dioxide as a gas, or with any constituents capable of reacting to form an acid gas. For example, foaming could be achieved by mixing yeast and sugar to form carbon dioxide and ethanol.

A person familiar with the different foaming methods can easily adapt more conventional foaming methods such as the use of mechanical mixers, bubbling or chemical foaming.

Drying the Gelled Foam The method according to the invention can also implement drying the gelled foam obtained at step b, by means of any method known to those skilled in the art. The drying can, for example, be carried out in the open air or by freeze-drying.

Using Gelled Foam

The gelled polysaccharide foam obtained from the method according to the present invention is preferably intended to be applied to the skin, wounds, skin appendages or mucous membranes. It can advantageously be used on wounds, burns or scars (whether they are linked to an accident, an illness or to the consequences of a surgical intervention), and finds a particularly interesting application in cavity wounds. Indeed, the foam according to the invention can be applied with a simple and rapid gesture, and will conform to the wound bed.

The present invention is further illustrated in the following non-limiting example.

EXAMPLE

Example 1

A mixture based on alginate and calcium ion complexed with EGTA as a chelating agent (total volume of 400 mL) was prepared.

To this end, the calcium ion was first complexed with EGTA: 5.88 g of $CaCl_2$, $2H_2O$ (divalent cation) were mixed and 15.2 g of EGTA were added to 400 mL of ultra pure water (MilliQ). The solution is stirred using a magnetic stirrer.

Since the pH is then close to 2, the chelating agent EGTA does not dissolve. The pH is raised by slow addition of sodium hydroxide (NaOH) pellets until pH 7 is reached. The solution becomes clear at a pH of about 4 due to the dissolution of EGTA and the association thereof with calcium ions Ca2+.

3.02 g of high molecular weight alginate (368,900 Da) and 9.21 g of low molecular weight alginate (84,430 Da) are slowly dissolved in this calcium-EGTA solution at a temperature of 50° C. using mechanical stirring. 1.01 g of Saponin (from Quillaja Saponaria Molina) are then added as a surfactant, with gentle stirring so as to avoid untimely foaming during the dissolution of the surfactant. Once the alginate has dissolved well, the pH of the solution is adjusted if necessary to between 7 and 8.

The mixture is then poured into a 1 L whipped cream siphon. An 8 g $N_2O$ capsule is built into the system, holding the siphon upside down. Another 8 g capsule of $CO_2$ is then added and the system is mixed well before the siphon is activated to proceed with the foaming.

The foam solidifies in less than 5 min. It is homogeneous, stable over time, has good mechanical strength and good absorption capacity.

Example 2

A mixture based on alginate and calcium ion complexed with EGTA was prepared as in Example 1, but using a syringe system (maximum total volume of foam: 60 mL).

To this end, 12 mL of a 0.5% by weight solution of alginate, 0.03 mol/L of $CaCl_2.2H_2O$ (divalent cation) and 0.5% by weight of EGTA were prepared.

12 mL of the alginate solution is introduced into a 60 mL syringe, connected by a tube to a second syringe containing air, and a third syringe containing $CO_2$ (total gas volume: 48 mL).

The alginate solution is foamed by passing the solution and the gas(es) from one syringe to the other repeatedly, until the foam obtained is homogeneous.

Different foams were obtained by varying the volumes of air and carbon dioxide:

TABLE 1

| Valg/mL | Air/mL | $VCO_2$/mL | $VCO_2$/(Vair + $VCO_2$) | Perfluorohexane |
|---------|--------|------------|--------------------------|-----------------|
| 12 | 48 | 0 | 0 | no |
| 12 | 28 | 20 | 0.42 | no |
| 12 | 18 | 30 | 0.63 | no |
| 12 | 0 | 48 | 100 | no |
| 12 | 0 | 48 | 100 | yes |
| 12 | 48 | 0 | 0 | yes |

Foams containing $CO_2$ are homogeneous, stable over time, have good mechanical resistance and good absorption capacity. Foams that do not contain $CO_2$ do not solidify and drain quickly. The presence of perfluorohexane makes it possible to improve the stability over time of the obtained foams.

The invention claimed is:

1. A method for the preparation of a gelled polysaccharide foam comprising the following steps:
   (a) the preparation of a mixture comprising:
   at least one solubilized polysaccharide chosen from alginates, pectic substances, carrageenans, and mixtures thereof
   at least one solvent of said polysaccharide,
   at least one ionic crosslinking agent of said polysaccharide, the crosslinking agent being not available,
   optionally at least one plasticizer soluble into said solvent,
   optionally at least one surfactant, and
   optionally at least one additive,
   (b) foaming and gelling said mixture prepared at step (a) by incorporating a pH modifying gas, and
   (c) optionally drying the gelled foam obtained at step (b).

2. The method according to claim 1, wherein the at least one solubilized polysaccharide is an alginate.

3. The method according to claim 1, wherein the at least one solubilized polysaccharide is present in an amount of 0.5% to 10% by weight, relative to the total weight of the mixture.

4. The method according to claim 1, wherein the at least one ionic crosslinking agent is at least one polyvalent cation.

5. The method according to claim 1, wherein the at least one ionic crosslinking agent is a bivalent ion in chelated form.

6. The method according to claim 1, wherein the at least one ionic crosslinking agent is present in an amount of 0.1% to 15% by weight, relative to the total weight of the mixture.

7. The method according to claim 1, wherein the at least one solvent is an inorganic solvent.

8. The method according to claim 1, wherein the at least one solvent is present in an amount of 50% to 99% by weight, relative to the total weight of the mixture.

9. The method according to claim 1, wherein the at least one surfactant is a nonionic or anionic surfactant.

10. The method according to claim 1, wherein the at least one surfactant is present in an amount of 0.01% to 10% by weight, relative to the total weight of the mixture.

11. The method according to claim 1, wherein the at least one additive is an active agent.

12. The method according to claim 1, wherein the at least one additive is present in an amount of 0.5% to 20% by weight, relative to the total weight of the mixture.

13. The method according to claim 1, wherein the pH-modifying gas is an acid gas.

14. The method according to claim 1, wherein step (b) is implemented by incorporating a mixture of said acid gas with an inert gas.

15. A gelled polysaccharide foam obtained from the method according to claim 1.

16. A method of controlling release of active agents in food or cosmetics field, comprising adding a polysaccharide gel foam according to claim 15 to a food or cosmetic.

17. A method for treating wounds comprising applying to the wounds a polysaccharide gel foam according to claim 15.

18. The method for treating wounds according to claim 17, wherein the wounds are selected from the group consisting of cavity wounds, venous ulcers, diabetic foot ulcers, and pressure ulcers.

19. The method according to claim 1, wherein the ionic crosslinking agent is at least one bivalent cation or trivalent cation.

20. The method according to claim 1, wherein the pH-modifying gas is an acid gas selected from the group consisting of carbon dioxide, sulfur dioxide, nitrogen oxide, and a mixture thereof.

* * * * *